(12) United States Patent
Sughrue et al.

(10) Patent No.: US 11,694,806 B2
(45) Date of Patent: Jul. 4, 2023

(54) SYSTEMS AND METHODS FOR GROUPING BRAIN PARCELLATION DATA

(71) Applicant: Omniscient Neurotechnology Pty Limited, Sydney (AU)

(72) Inventors: Michael Edward Sughrue, Brighton le Sands (AU); Stephane Philippe Doyen, Mount Kuring Gai (AU); Hugh Monro Taylor, Point Piper (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/531,697

(22) Filed: Nov. 19, 2021

(65) Prior Publication Data

US 2023/0162855 A1 May 25, 2023

(51) Int. Cl.
| | | |
|---|---|---|
| *G16H 50/20* | (2018.01) | |
| *G16H 10/60* | (2018.01) | |
| *G16H 30/40* | (2018.01) | |
| *G16H 80/00* | (2018.01) | |
| *G16H 40/67* | (2018.01) | |

(Continued)

(52) U.S. Cl.
CPC ............. *G16H 50/20* (2018.01); *G16H 10/60* (2018.01); *G16H 20/70* (2018.01); *G16H 30/40* (2018.01); *G16H 40/63* (2018.01); *G16H 40/67* (2018.01); *G16H 80/00* (2018.01)

(58) Field of Classification Search
CPC ........ G16H 50/20; G16H 40/67; G16H 10/60; G16H 30/40; G16H 40/63; G16H 20/70; G16H 80/00
See application file for complete search history.

(56) References Cited

U.S. PATENT DOCUMENTS

| 11,055,849 B2 | 7/2021 | Sughrue et al. |
| 11,145,119 B2* | 10/2021 | Sughrue et al. |
| 2015/0227702 A1* | 8/2015 | Krishna et al. |

(Continued)

FOREIGN PATENT DOCUMENTS

| KR | 10-1754291 | 7/2017 |
| KR | 10-2313658 | 10/2021 |

OTHER PUBLICATIONS

International Search Report and Written Opinion in International Appln. No. PCT/AU2022/051263, dated Jan. 27, 2023, 11 pages.

*Primary Examiner* — Michael Tomaszewski
*Assistant Examiner* — William T. Monticello
(74) *Attorney, Agent, or Firm* — Fish & Richardson P.C.

(57) ABSTRACT

Methods, systems, and apparatus, including computer programs encoded on computer storage media, for grouping brain parcellation data. One of the methods includes receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

20 Claims, 6 Drawing Sheets

(51) Int. Cl.
    *G16H 40/63*     (2018.01)
    *G16H 20/70*     (2018.01)

(56) References Cited

U.S. PATENT DOCUMENTS

| | | |
|---|---|---|
| 2016/0302689 A1 | 10/2016 | Kang et al. |
| 2017/0043167 A1* | 7/2017 | Widge et al. |
| 2017/0273650 A1* | 9/2017 | Ono et al. |
| 2018/0314691 A1* | 11/2018 | Mori et al. |
| 2019/0167179 A1* | 10/2019 | Arzy |
| 2020/0005932 A1* | 1/2020 | Butz-Ostendorf et al. |
| 2020/0167912 A1* | 5/2020 | Xu et al. |
| 2020/0288980 A1* | 9/2020 | Stern et al. |
| 2021/0282697 A1 | 9/2021 | Lee |
| 2021/0401289 A1* | 12/2021 | Yamashita et al. |
| 2022/0262515 A1* | 8/2022 | Jirsa et al. |

\* cited by examiner

SYSTEMS AND METHODS FOR GROUPING BRAIN PARCELLATION DATA

BACKGROUND

Technical Field

The present disclosure relates generally to grouping brain parcellation data based on one or more brain functions, displaying the grouped parcellation data, and allowing user interaction with the displayed data. The present invention also relates to a system, method, and apparatus for grouping brain parcellation data based on one or more brain functions, displaying grouped parcellation data, and allowing user interaction with the displayed data, and to a computer program product including a computer readable medium having recorded thereon a computer program for grouping brain parcellation data based on one or more brain functions, displaying grouped parcellation data, and allowing user interaction with the displayed data.

Background

Medical imaging of a brain can provide insights into functional activity and structural connections of a brain. Images generated using medical imaging techniques such as magnetic resonance imaging (MRI) can be used to provide visual representations of structural and functional data of the brain which can facilitate biomedical research, clinical analysis, and medical interventions.

SUMMARY

This specification describes technologies for grouping brain parcellation data based on one or more specified brain functions and/or displaying the grouped brain parcellations in a user-interactive brain navigation system (e.g., a graphical user interface). The grouped parcellations can be used to localize regions that are associated with particular brain functions and allow visualization of the grouped parcellation data in relation to brain anatomy.

The disclosed technologies can be used by clinicians, other medical professionals, or users to gain insights about structures, function, and their relationship in a subject's brain. Based on such insights, the clinicians, other medical professionals, or users can perform improved and more informed diagnosis, treatments, operations, research, or their combinations than with existing systems.

For example, the disclosed technology can allow a user to group parcellation data of the brain in a customized and meaningful way, e.g., grouping parcellations that are related to a specific symptom, a mood, a disease, or a cognitive function. A subject's brain can be represented by a brain atlas which can include a set of three-dimensional (3D) voxels representing at least a portion of the brain, each voxel can be assigned to one of the parcellations in a parcellation scheme. The parcellation scheme can be described in a coordinate space. The coordinate space can be, for example, the Montreal Neurologic Institute (MNI) space. The term "parcellation" can refer to the process of delineating regions of the brain that have similar properties between individuals, such as functional activity, cytoarchitecture, and structural connectivity. The "parcel" can be a region of the brain (e.g., cortex) that can be shown to have similar properties across individuals, even if the exact boundaries may differ. Parcellating a brain can be a useful mechanism for analyzing neuroimaging data because it can reduce complexity of the brain's activity to a finite number of domains, and such domains can be assumed to have relatively uniform functions. In some cases, "parcellation" and "parcel" are used as interchangeable terms herein.

A parcellation or a group of parcellations can be associated with different brain functions at one or more specified grouping levels. For example, a given parcellation can be associated with cognitive brain functions at a first grouping level, and with memory or language at a second lower grouping level with more refined or more specific subgroups. The capability to relate parcellation(s) to a brain function or other brain characteristics, like a symptom or a disease, can provide medical professionals with a helpful tool in understanding brain parcellations, their connections with each other, and their role(s) in a brain's function thereby facilitating neuropsychological research and treatment and neurosurgical interventions. As such, there is a need for technologies that enable grouping parcellation data with different grouping categories and/or levels in relation to a brain function or characteristics to make parcellation information convenient, efficient, and less complicated to analyze or use by different users.

In general, one innovative aspect of the subject matter described in this specification can be embodied in methods that include the actions of: receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As additional description to the embodiments described below, the present disclosure describes the following embodiments.

Embodiment 1 is a method, comprising: receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

Embodiment 2 is the method of embodiment 1, wherein the brain function category is one or more selected from: an emotion, scholastic ability, a brain disease symptom, ability to perform one or more predetermined types of work, and an answer to one or more clinical questions.

Embodiment 3 is the method of embodiments 1 or 2, wherein taking the action based on the determined subset of the brain parcellation data comprises: forwarding the determined subset of the brain parcellation data for display at a user device; receiving an export request of the determined subset of the brain parcellation data; or both.

Embodiment 4 is the method of any one of embodiments 1 to 3, wherein taking the action based on the determined subset of the brain parcellation data comprises: analyzing the determined subset of the brain parcellation data; and allowing a user to make a recommendation regarding a treatment based on the analysis of the determined subset of the brain parcellation data.

Embodiment 5 is the method of any one of embodiments 1 to 4, wherein taking the action based on the determined subset of the brain parcellation data comprises: analyzing the determined subset of the brain parcellation data; and making a recommendation regarding a treatment based on the analysis of the determined subset of the brain parcellation data.

Embodiment 6 is the method of any one of embodiments 1 to 5, the brain parcellation data for the subject comprises a plurality of parcellations, and wherein the plurality of parcellations are spatially registered to brain anatomical data of the subject.

Embodiment 7 is the method of any one of embodiments 1 to 6, the set of functions within the brain function category comprises a hierarchy of multiple levels, and each level comprises one or more brain functions in the set of functions.

Embodiment 8 is the method of any one of embodiments 1 to 7, wherein a first brain function on a first level in the hierarchy comprises at least a second brain function on a second level lower than the first level.

Embodiment 9 is the method of any one of embodiments 1 to 8, wherein the brain function category is selected from: response to threat, fear, stress, anxiety, and reward.

Embodiment 10 is the method of any one of embodiments 1 to 9, wherein the brain parcellation data for the subject comprises a brain atlas of the subject.

Embodiment 11 is the method of any one of embodiments 1 to 10, wherein the threshold is determined based on expert knowledge of healthy brains, diseased brains, or both.

Embodiment 12 is the method of any one of embodiments 1 to 11, wherein the determined subset of the brain parcellation data comprises one or more parcellations within the brain parcellation data; and corresponding spatial information of the one or more parcellations within a brain of the subject.

Embodiment 13 is the method of any one of embodiments 1 to 12, wherein forwarding the data for display comprises sending the data for display using a graphic user interface, and wherein the selection from the user of the brain function from the set of functions within the brain function category is made by using the graphic user interface.

Embodiment 14 is a computer program product, encoded on one or more non-transitory computer storage media, comprising instructions that when executed by one or more computers cause the one or more computers to perform operations comprising: receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

Embodiment 15 is one or more non-transitory computer storage media encoded with computer program instructions that when executed by one or more computers cause the one or more computers to perform operations comprising: receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

Embodiment 16 is a system comprising: one or more computers and one or more storage devices on which are stored instructions that are operable, when executed by the one or more computers, to cause the one or more computers to perform operations comprising: receiving brain parcellation data for a subject; receiving an indication from a user of a brain function category; forwarding data for display, the data comprising a set of functions within the brain function category; receiving a selection from the user of a brain function from the set of functions within the brain function category; determining a subset of the brain parcellation data for parcellations that have an overlap with the selected brain function where the overlap exceeds a threshold; and taking an action based on the determined subset of the brain parcellation data for parcellations that have an overlap with the selected brain function where the overlap exceeds a threshold.

Present systems or methods may generate parcellations or present individual parcellations without showing any associations between parcellations or connections from parcellations to a specific brain function or characteristics. Such existing systems or methods can be cumbersome to use and typically produce outputs that lack clinical usefulness. The subject matter described herein can be implemented in particular embodiments so as to realize numerous advantages over existing systems and methods. For example, the disclosed technologies can provide a technical solution for medical professionals or other users to the technical problem of grouping parcellations in various clinically useful categories, at different group levels, with an easy-to-use interface that allows users to glean insights about parcellations and their role(s) in the brain's function. The interface can be an interactive, user-friendly graphical user interface (GUI) that facilitates customized visualization of the grouping information.

The disclosed technologies can process parcellations of the brain and output groupings of them with convenient customization for visualization. For example, the subject matter herein advantageously allows simultaneous visualization of 1) spatial locations of grouped parcellations relative to anatomical structures in the brain, e.g., spatial relationship of the parcellations relative to brain structure(s) that are in question, e.g., in a planned surgical procedure, and 2) location information of a parcellation within a group relative to the other parcellations within the same group. Further, the subject matter herein allows grouping based on various grouping categories and at different levels in a consistent manner. For example, a grouping category can be cognitive functions and such category can include multiple functions such as memory and language. The grouping category can also be based on brain diseases and various symptoms. As another example, a grouping category can be scholastic abilities, and such category can include multiple functions at a first level, such as problem solving, language, organization, collaboration, science, technology, engineering, and mathematical (STEM) abilities. The "language" function can then, at a second level, include different functions such as fluency, reading, and writing. As such, the claimed subject matter advantageously allow presentation of a parcellation or a set of parcellations to a user from different angles with consistency. In other words, the same parcellations can be grouped differently in multiple groups according to different grouping category and/or grouping levels, which can enable medical professionals to make informative inferences and decisions based on such information.

The grouping of parcellations and visualization of groupings can also provide the user a comprehensive understanding of the subject's brain functionality. As a result, the disclosed technologies can enable a medical professional to make clinical determinations by visualization of the grouping of parcellation data. The disclosed technologies can be used to: understand the nature of a neurologic deficit in a subject; guide a surgical procedure; select appropriate target(s) in a brain for a therapy; and validate analysis or methods by cross referencing against parcellation groupings at various grouping levels. For example, a medical professional can gain insight about parcellations of a patient's brain that are associated with generating a mood or an emotion. Such information can be used to determine a treatment that may help target the specific parcellations in treatment of neuropsychological diseases like depression.

The details of one or more variations of the subject matter described herein are set forth in the accompanying drawings and the description below. Other features and advantages of the subject matter described herein will be apparent from the description, drawings, and claims.

BRIEF DESCRIPTION OF THE DRAWINGS

Like reference symbols in various drawings indicate like elements.

DETAILED DESCRIPTION

A brain mapping system can segment a subject's brain into areas providing an organizational structure for investigating the brain. However, when it comes to interpreting what these areas do, limitations can be faced if that knowledge is not readily available. Systems and methods described in this specification reduce that complexity by providing various useful grouping of brain regions, e.g., parcellations. For instance, a set of parcellations can be grouped according to a cognitive ability (e.g., working memory) or a symptom (e.g., delusion) or any other relevant grouping (e.g., mathematical abilities). Additionally to this a specific type of grouping can use the research domain criteria (RDoC) framework which provides a symptom-based classification of mental illness.

Figure 1:
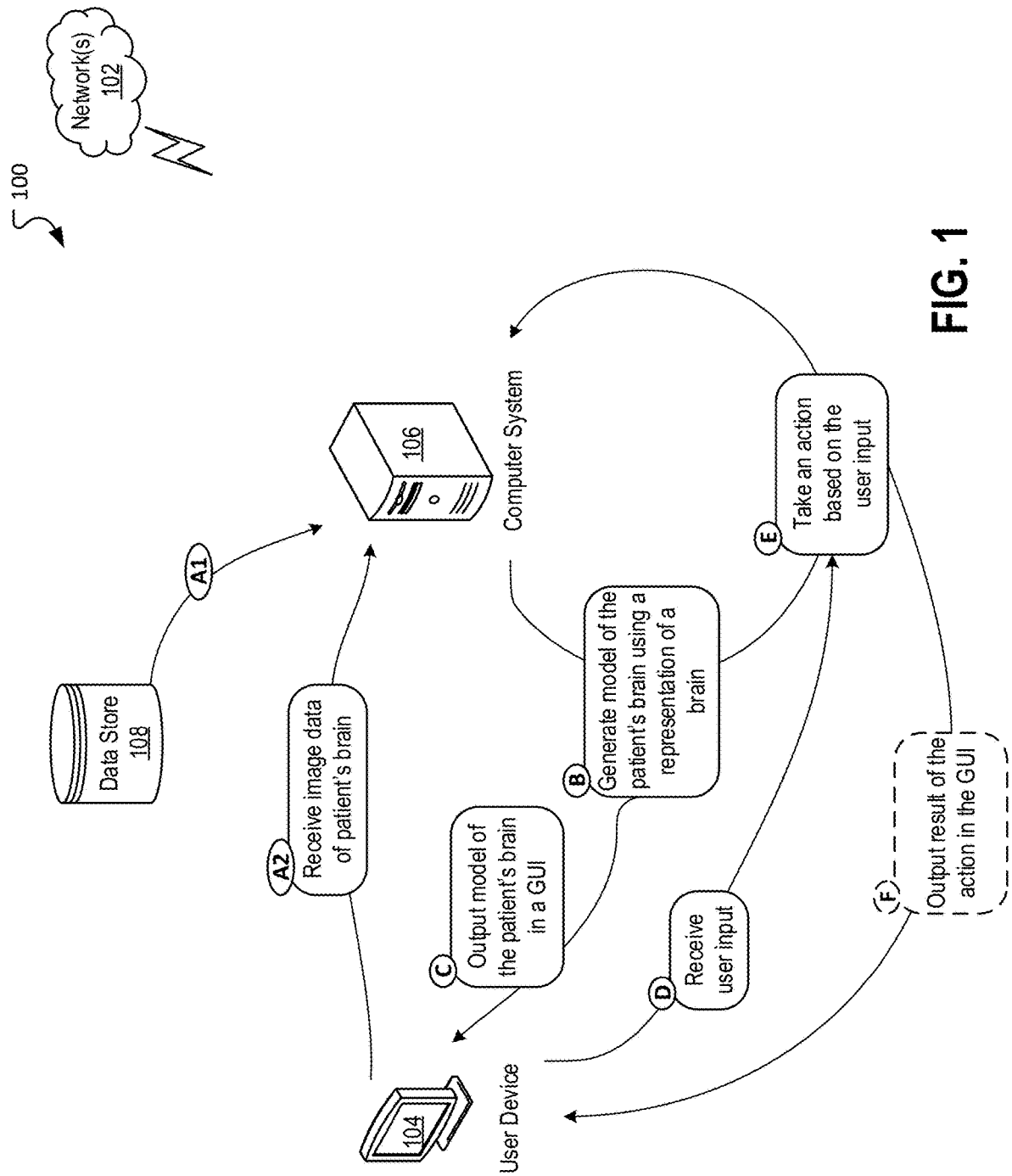
FIG. 1 is a conceptual diagram illustrating a computing environment for generating a GUI representation of a brain.

FIG. 1 is a schematic diagram illustrating a computing environment 100 for generating a display of brain data, e.g., via a GUI. The computing environment 100 can include a user device 104, a computer system 106, a data store 108, and a medical imaging device 110, which can communicate (e.g., wired and/or wirelessly) via network(s) 102.

The user device 104 can be used by a medical professional, such as a clinician, surgeon, doctor, nurse, researcher, or other professional. The user device 104 and technologies described herein can be used by any other user. The user device 104 can be any one of a computer, laptop, tablet, mobile device, mobile phone, and/or smartphone. Sometimes, the user device 104 can be integrated into or otherwise part of one or more other devices in a medical setting, such as the medical imaging device 110 and/or the computer system 106. The user can use the user device 104 to view information about the brain. For example, using the disclosed technology, the user can view, at the user device 104, three dimensional (3D) representations of the brain and make determinations about what diagnosis, treatment, and/or surgical procedures to perform. The user can also view other/additional information about the particular patient at the user device 104 to make more informed decisions with regards to the particular patient's diagnosis, treatment, surgery, or other medical or research purposes. Thus, the user device 104 can provide hardware that can support the GUIs, software, and applications described herein, such as a singular and interactive brain navigation system that makes it easier and more intuitive for the medical professionals to make medical and research determinations.

The computer system 106 can be a remote computing system, a cloud-based system or service, and/or integrated with or otherwise part of one or more devices in a medical setting (e.g., such as the user device 104 and/or the medical imaging device 110). The computer system 106 can be a computer, processor, a network of computers, a server, and/or a network of servers. Sometimes, each medical setting (e.g. a hospital) can have one or more computer systems 106. Sometimes, the computer system 106 can be used across multiple medical settings (e.g., multiple hospitals). The computer system 106 can be configured to generate interactive representations of patients' brains based on image data of the brains. The computer system 106 can also generate GUIs to display the interactive representations of the brains at the user device 104.

Sometimes, the computer system 106 can modify the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 108 for future retrieval and use. Removing personally identifying information can also be advantageous if the computer system 106 is remote from the user device 104 and the interactive representations of the brain are generated at the computer system 106 that is outside a secure hospital infrastructure or other network where the image data is generated and/or the representations of the brain are displayed. In other words, removing personally identifying information can be advantageous to preserve patient privacy when patient data is communicated between different networks and/or infrastructure.

The data store 108 can be a remote data store, cloud-based, or integrated into or otherwise part of one or more other components in the medical setting (e.g., such as the user device 104 and/or the computer system 106). The data store 108 can store different types of information, including but not limited to image data of patient brains (e.g., from the medical imaging device 110), cleaned image data (e.g., from the computer system 106), data for use in creating 3D representations of patient brains or other interactive representations of patient brains (e.g., from the computer system 106), connectivity data associated with patient brains, determinations, actions, or other user input taken by the medical professional (e.g., at the user device 104), patient information or records, or other relevant information that can be used in a medical setting.

The medical imaging device 110 can be any of a variety of devices and/or systems that are used in the medical setting to capture image data of patient brains. The medical imaging device 110 can capture image data that includes but is not limited to x-ray data, computed tomography (CT) scans, magnetic resonance imaging data (MRIs), Near-infrared spectroscopy (NIRS) data and/or Electroencephalography (EEG) data. The computer system 106 can be configured to receive a variety of image data of a brain and generate parcellation data about the brain from that image data to map the data onto a user-friendly interactive representation of the brain.

Figure 2:
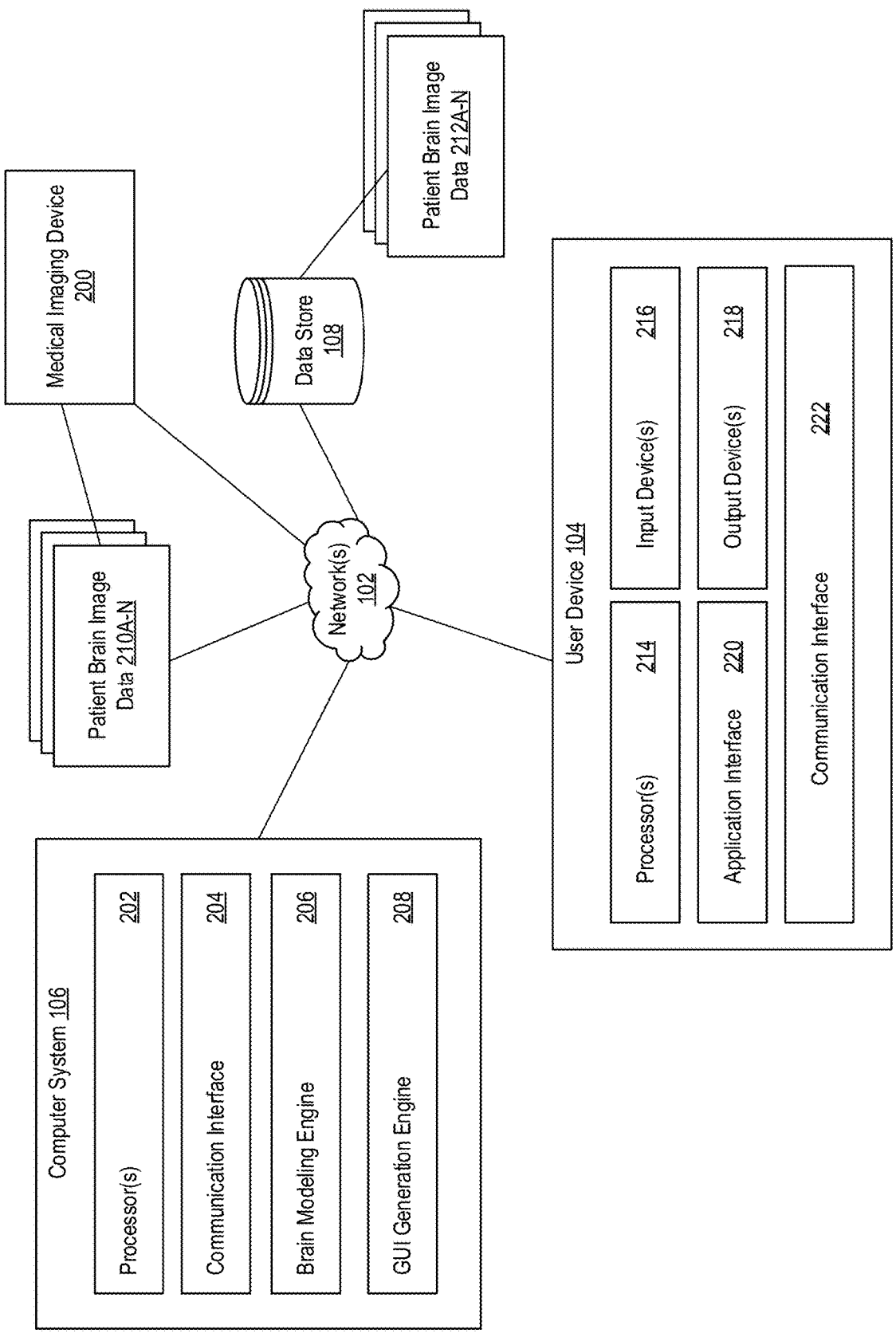
FIG. 2 illustrates components in a computing landscape that can be used to generate the GUI representation of the brain.

Referring to FIGS. 1 and 2, the computer system 106 can receive image data of the brain from one or more of the data store 108 (step A1), the user device 104 (step A2), and the medical imaging device 200. Sometimes, for example, when the user device 104 is part of the medical imaging device 200, the computer system can receive the image data captured by the medical imaging device 200 from only one device (e.g., the medical imaging device 200 or the user device 104). The image data can be captured by the medical imaging device 200 then sent directly, in real-time, to the computer system 106 for real-time processing. Sometimes, the image data can be captured by the medical imaging device 200, then initially reviewed by the medical professional at the user device 104. Accordingly, the user device 104 can transmit the image data to the computer system 106 (step A2).

In some implementations, image data of multiple different brains can be captured by multiple different medical imaging devices 200. The image data can be stored in the data store 108 for future processing and analysis. The computer system 106 can then retrieve a batch or batches of the image data from the data store 108 and batch process the image data. Batch processing can be advantageous to use fewer computational resources and reduce network bandwidth.

Once the computer system 106 receives the image data (e.g., steps A1-A2), the computer system can generate a model of the brain using a representation of a brain (step B). For example, the computer system 106 can map or model the patient's brain from the image data onto a 3D representation of a brain. The 3D representation can be a generic brain in 3-dimensional or other multi-dimensional space or it can be an anatomical representation of the particular patient's brain. The 3D representation can be a glass brain, e.g., showing 3D anatomical structures derived from medical images with a preset degree of transparency which facilitates superimposing parcellations in their anatomically accurate locations. Mapping the patient's brain onto the glass brain can be advantageous to provide vantage points of different structures, parcellations, groups of parcellations, and connectivity in the particular patient's brain. A medical professional can more easily analyze the particular patient's brain via the 3D representation of the brain rather than through the raw image data captured by the medical imaging device 110. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 106 can output the model of the patient's brain to a GUI at the user device 104 (step C). For example, the computer system 106 can generate GUI data representing a model of the patient's brain and then transmit the GUI data to the user device 104 to be processed for display. The model can represent the patient's brain overlaid on the glass brain. Sometimes, instead of displaying the model at the user device 104 (step C), the computer system 106 can store the model of the patient's brain in the data store 108. The model of the patient's brain can then be accessed/retrieved at a later time and presented to a medical professional or other user at the user device 104.

As mentioned throughout, when the model of the patient's brain is displayed at the user device 104, the GUI can allow the medical professional to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is displayed at the user device 104. The medical professional can change views of the model of the patient's brain (e.g., rotate around the model or view only a left or right side of the patient's brain), select portions of the patient's brain from the model (e.g., select a particular lobe, node, parcellation, group of parcellation such as a group of parcellations that form a functional network), view other information about the patient (e.g., health records, prior medical visits, etc.), and simulate surgical procedures that can impact different parcellations, groups of parcellations, or portions of the patient's brain (e.g., slicing a node or nodes that are connected to other nodes in the patient's brain). The medical professional can provide input to the user device 104, for example, via an input device, and the input can indicate the medical professional's interaction(s) with the model of the patient's brain. This input can then be received by the computer system 106 (step D).

The computer system 106 can take an action based on the received user input (step E). For example, if the medical professional changes or selects a different view of the model of the patient's brain, then the computer system 106 can generate an updated GUI data representing the patient's brain that includes the selected view data. This updated GUI data can be processed for display at the user device (step F). As another example, the medical professional can remove one or more parcellations or group(s) of parcellations from the model of the patient's brain. The computer system 106 can receive this input (step D), simulate removal of the user-selected nodes (step E), then output results of removing such parcellations or group(s) of parcellations from the brain at the user device 104 (step F). The medical professional can review the output results and take further actions in response. Further actions can include decisions about what parcellations or group of parcellations the medical professional should remove during the actual medical procedure and/or how to proceed with diagnosis, treatment, and/or the medical procedure.

Sometimes, the computer system 106 can take an action based on the user input (step E) that does not also include outputting a result of the action at the user device 104 (step F). For example, the medical professional can input notes about what actions the medical professional intends to take during a medical procedure, a diagnosis for the particular patient, and/or treatment for the patient. The computer system 106 can receive this input and store it in the data store 108 but may not output results from storing this input. This input can then be retrieved from the data store 108 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 106 can take one or more other actions based on the user input (step E) and optionally output results of the action(s) at the user device 104 (step F).

FIG. 2 illustrates components in a computing landscape that can be used to generate data about the brain. As described above, the user device 104, computer system 106, data store 108, and medical imaging device 110 can communicate via the network(s) 102. One or more of the components 104, 106, 108, and 110 can also be integrated into a computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 106 can include processor(s) 202, communication interface 204, brain modelling engine 206, and GUI generation engine 208. The processor(s) 202 can be configured to perform one or more operations described herein. Although not depicted, the computer system 106 can also include at least one memory unit, which may have semiconductor random access memory (RAM) and semiconductor read only memory (ROM).

One or more of the techniques and processes described herein can be implemented as software application programs executable by the processor(s) 202 in the computer system 106. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 106. For example, steps for any of the techniques and processes described herein can be affected by instructions in the software application programs that are carried out within the computer system 106. Software instructions may be formed as one or more code modules (e.g., using PYTHON or equivalent language modules installed on the computer system 106 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 104.

Moreover, the software may be stored in a non-transitory, tangible, computer readable medium, including storage devices described throughout this disclosure. The software can be loaded into the computer system 106 from the computer readable medium, and then executed by the computer system 106. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on websites and the like.

Still referring to the computer system 106, the brain modelling engine 206 can be configured to map a patient's brain onto a representation of a brain (e.g., refer to step B in FIG. 1). For example, the brain modelling engine 206 can receive patient brain image data 210A-N, which can be used to generate a model of the patient's brain. The patient brain image data 210A-N can be received from the medical imaging device 110. The patient brain image data 210A-N can also be received from the user device 104. In some implementations, as described in reference to FIG. 1, the computer system 106 can retrieve patient brain image data 212A-N from the data store 108. The patient brain image data 212A-N can then be used by the brain modelling engine 206 to model the patient's brain.

Sometimes, modelling the brain can include identifying parcellation data for the particular brain. Modelling the brain can then include mapping the parcellation data over the representation of a generic brain. In yet some implementations, modelling the patient's brain can include identifying parcellations, groups of parcellations, and other portions of the patient's brain that can be mapped onto the representation of the generic brain. Moreover, the brain modelling engine 206 can be configured to identify personal information in the image data of the brain and extract that information before mapping the patient's brain onto the representation of the generic brain. The brain modelling engine 206 can use one or more machine learning models to accurately map the particular patient's brain data onto a representation of the generic brain.

In some implementations, for example, digital imaging and communications in medicine (DICOM) images of a particular brain to be parcellated can be processed by the brain modelling engine 206. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project (HCP) can be determined, and diffusion tractography of the DICOM images can be performed to determine a set of whole brain tractography images of the particular brain (in neuroscience, tractography can be thought of as a 3D modelling technique used to represent tracts, e.g., to represent white matter tracts visually). For each voxel in a particular parcellation in the registered atlas, the following method can be performed: determining, using tractography vectors showing connectivity of a voxel with other voxels in other parcellations, classifying the voxel based on the probability of the voxel being part of the particular parcellation; and repeating determining the voxel level tractography vectors and classifying the voxels for many parcellations, e.g., all parcellations of the human connectome project multi-modal parcellation version 1.0 (HCP-MMP1) Atlas, to form a personalized brain atlas (PBs Atlas) containing an adjusted parcellation scheme reflecting the particular brain. The related details are described in U.S. Pat. Nos. 11,055, 849 and 11,145,119 and incorporated herein by reference in their entirety.

The GUI generation engine 208 can be configured to generate GUI data for the modelled brain. The GUI generation engine 208 can receive the modelled brain data from the brain modelling engine 206 and generate appropriate GUI data for displaying the modelled brain data to a user, e.g., a medical professional (e.g., refer to FIG. 3). The GUI generation engine 208 can also transmit the generated GUI data to the user device 104 to be processed for display to the medical professional.

Moreover, whenever user input is received from the user device 104 that includes performing some action in response to the output model of the brain, the input can be received by the computer system 106. The brain modelling engine 206 can take some action (e.g., refer to step E in FIG. 1) in response to receiving the user input (e.g., refer to step D in FIG. 1). That action can include, for example, simulating removal of parcellations and/or group(s) of parcellations in the patient's brain. The GUI generation engine 208 can generate updated GUI data based on the actions taken by the brain modelling engine 206 (e.g., refer to step F in FIG. 1). The GUI generation engine 208 can then transmit the updated GUI data to the user device 104 to be processed for display to the medical professional.

Sometimes, one or more of the components of the computer system 106, such as the brain modelling engine 206 and the GUI generation engine 208 can be part of one or more different systems. For example, the brain modelling engine 206 can be part of a software application program that can be loaded and/or executed at another device, such as the user device 104 and/or the medical imaging device 110. As another example, the GUI generation engine 208 can be part of a software application program that is executed at the user device 104 and the brain modelling engine 206 can be executed at the computer system 106 or another remote computing system, server, or cloud-based server or system.

The user device 104 can include processor(s) 214, input device(s) 216, output device(s) 218, application interface 220, and communication interface 222. The processor(s) 214 can be configured to perform one or more operations described herein. Although not depicted, the user device 104 can also include at least one memory unit, which may have semiconductor random access memory (RAM) and semiconductor read only memory (ROM).

The input device(s) 216 and output device(s) 218 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 216 can be configured to receive user input from the medical professional or other user. The output device(s) 218 can be configured to output the model of the patient's brain and/or actions taken by the computer system 106 in response to the user input. The output device(s) 218 can present a variety of GUI displays and information to the medical professional, where such displays and information are generated by the computer system 106. The output device(s) 218 can also output information that is received or otherwise generated by the medical imaging device 110.

The application interface 220 can be executable software or another program that is deployed at the user device 104. The GUI data generated by the computer system 106 can be displayed or otherwise outputted via the application interface 220. In some implementations, the application interface 220 can be executed at a browser of the user device 104. The medical professional can then access and view the GUIs via the internet or other connection. Sometimes, the application interface 220 can be executed as a software module/program/product at the user device 104. The application interface 220 can provide the interactive GUIs to the medical professional and receive input from the medical professional (e.g., FIG. 3).

The communication interfaces 204 and 222 can be configured to provide communication between and amongst the components described herein. For example, a modem can be integrated therein.

Figure 3:
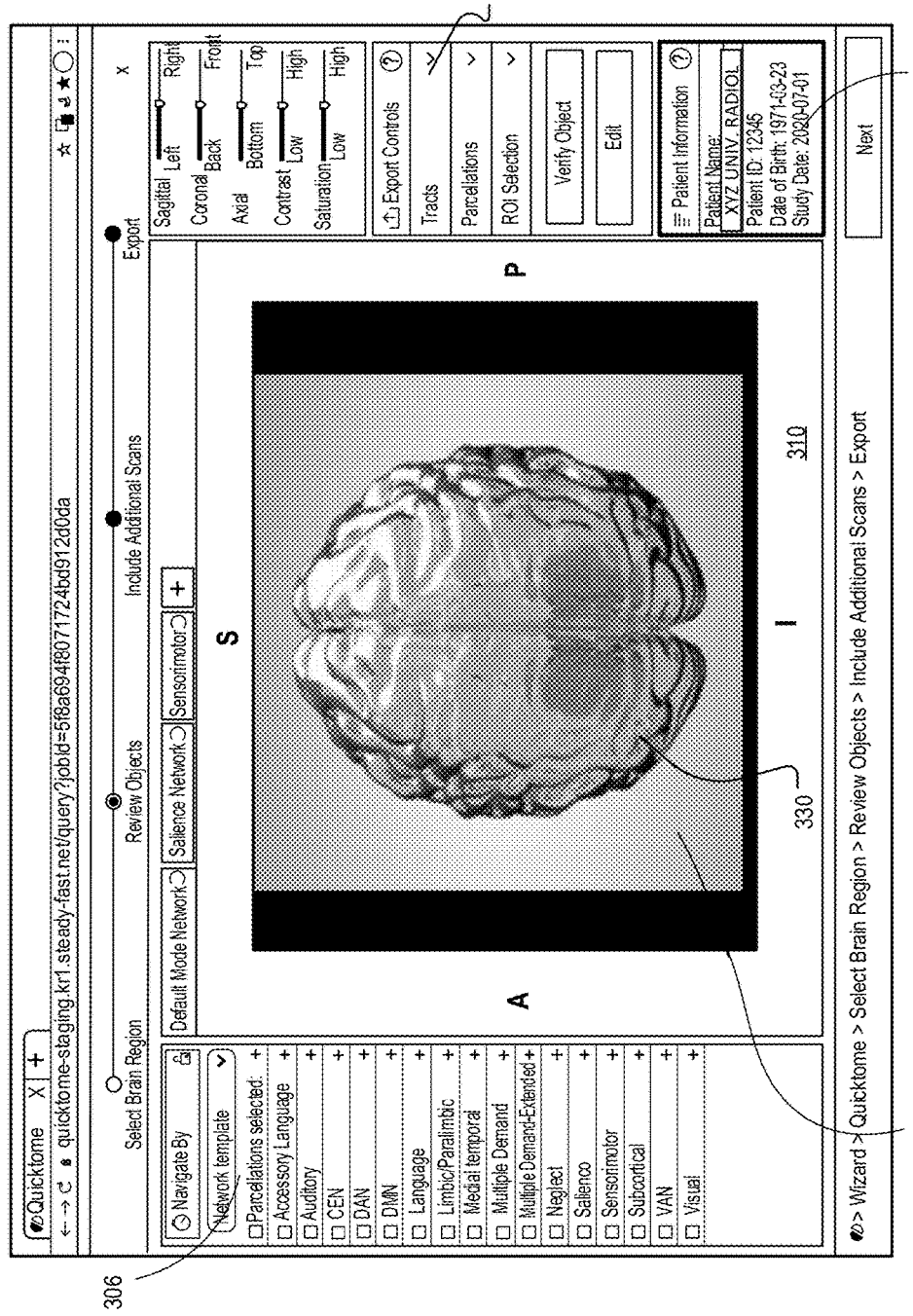
FIG. 3 illustrates an example user-interactive GUI displaying the brain.

FIG. 3 is an example user-interactive GUI. The GUI 300 can be displayed at the user device 104 described herein. The GUI 300 displays processed medical imaging data of a subject's brain within a data display window 310. The processed medical imaging data may be forwarded to a user device 104 by a server or another computer, e.g., the computer system 106 in FIG. 1. The processed medical imaging data may include processed data 302, patient information 304, and selectable options 306-307. The patient information can include but is not limited to age, gender, brain disease, treatment, and symptom(s).

The processed data 302 can include a 3D representation of the brain. Such representation can be generated from any type of medical imaging data that is indicative of anatomical information 330 of the brain. The processed data 302 can include anatomical data of some or all parts of the brain. At least a portion of the processed data 302 may have been processed from "raw" image data acquired at the medical imaging device(s) 110. The processing may include various manipulation or calculation of the "raw" image data, e.g., such as segmentation, registration, histogram, interpolation, filtering, and diffusion tensor calculation.

Figure 4:
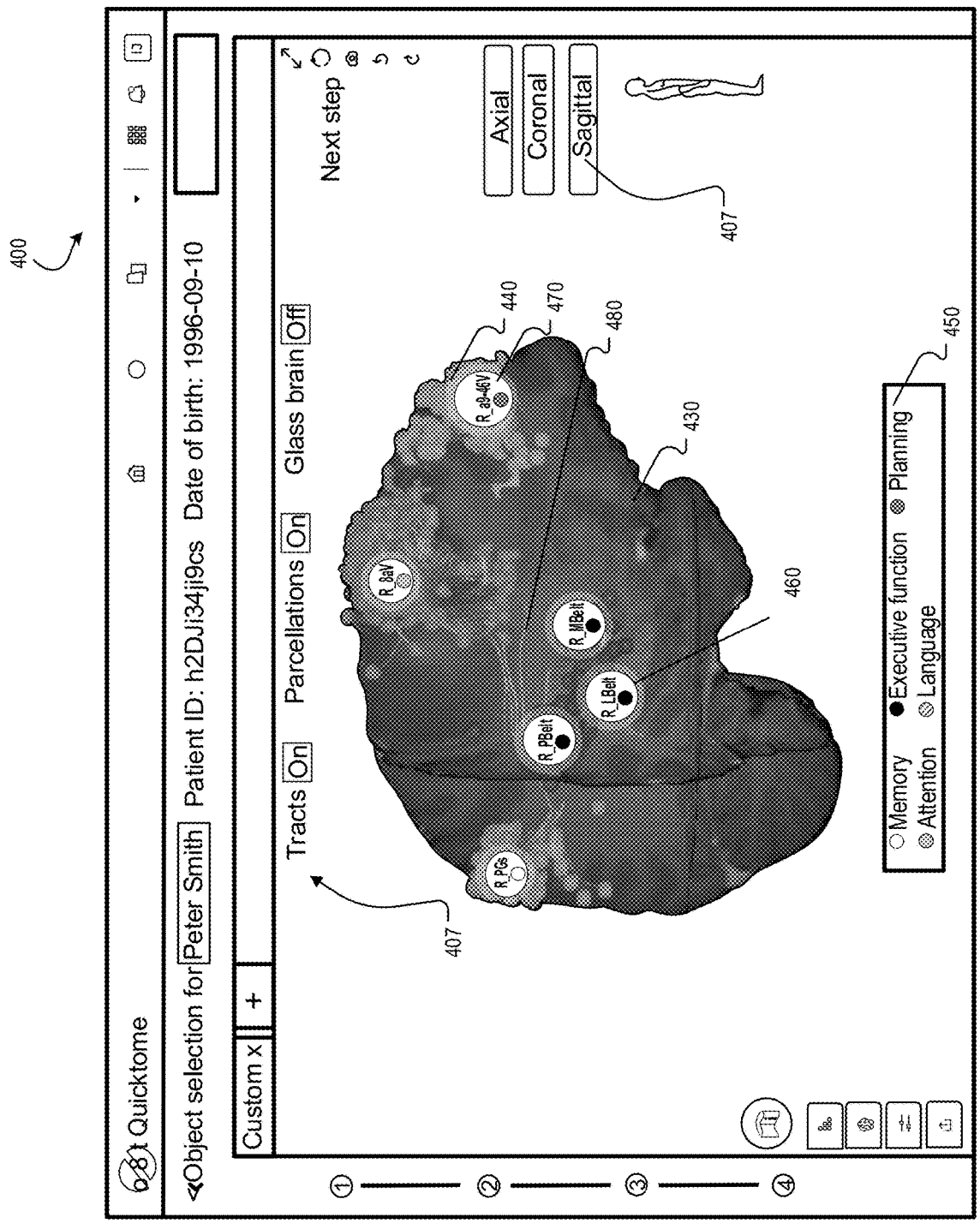
FIG. 4 illustrates an example user-interactive GUI displaying grouping of parcellations in a brain.

The processed data 302 may include parcellation data 440 in FIG. 4 for some or all parts of the brain. The parcellation data 440 may include, for one or more parcellations, a parcellation ID, a parcellation label, and MNI space coordinates, as shown in Table 1 below. Table 1 is described further below. The parcellation label and the parcellation ID can each be used as a unique identifier of the parcellation. Each parcellation may represent some predefined collection of brain tissue(s). A parcellation can include a single voxel in medical images or a group of voxels. When there are multiple parcellations in a group, they may or may not be spatially connected with one or more parcellations within the same group. In some cases, each parcellation may be visually represented using a size or shape that corresponds to the number of voxels or the size of brain tissues within it. For example, a parcellation represented by a bigger circle in the GUI indicates it is a parcellation with more voxels or tissues than a smaller circle representing another parcellation. In alternative cases, each parcellation may be visually represented by a uniform size and/or shape. A track can measure the functional connectivity between voxels, parcellations, or even groups of parcellations. A track may be visually represented by a line connecting two objects, e.g., parcellations, at its opposite ends. In some cases, the level of connectivity of the tracts may be visualized using different colors, patterns, or the like. The anatomical data 330 and the parcellation data 440 in FIG. 4 of the same brain can be spatially registered or aligned.

TABLE 1

Exemplary grouped parcellations.

| Group Name | Group Cluster ID | MNI | Parcellation ID | Parcellation Label | Percentage Overlap |
|---|---|---|---|---|---|
| fear_dmpfc | fear_dmpfc-insula cortex (anterior right) | 36 18 29 | 279 | R_IFJa | 48.37% |
| fear_dmpfc | fear_dmpfc-insula cortex (posterior right) | 36 −15 18 | 302 | R_OP2-3 | 33.82% |
| fear_dmpfc | fear_dmpfc-insula cortex (posterior right) | 36 −15 18 | 368 | R_Ig | 46.26% |
| fear_dmpfc | fear_dmpfc-parahippocampus (right) | 33 −18 −21 | 320 | R_H | 32.40% |
| potential_threat | potential_threat-Operculum-Insula | −44 12 2 | 108 | L_FOP4 | 26.44% |
| potential_threat | potential_threat-Insula | 36 20 −2 | 309 | R_MI | 21.70% |
| Reward_Anticipation | Reward_Anticipation-(L)_Insula | −30 26 4 | 111 | L_AVI | 26.30% |
| Reward_Anticipation | Reward_Anticipation-(R)_Insula | 33 29 4 | 369 | R_FOP5 | 31.72% |
| Reward_Anticipation | Reward_Anticipation-(L)_Caudate | −9 11 −2 | 426 | L_Accumbens | 25.98% |
| effort | effort-dACC | −3 11 34 | 58 | L_33pr | 27.18% |
| effort | effort-left striatum | −8 6 2 | 450 | R_Caudate | 32.48% |

Referring again to FIG. 3, the user, e.g., a medical professional, may interact with the processed data 302, the anatomical data 330, the parcellation data 340, and the selectable options 306-307 of the GUI 300. The selectable options 306-307 can be positioned around the data display window 310 of the GUI 300.

Although a brain image is useful for a user, the user can benefit more if they have additional information about components of the brain that is imaged. This additional information can be advantageous for the user to make more informed decisions with regard to diagnosis, treatment, research, and medical procedures. Accordingly, as shown in FIG. 3, the GUI 300 can provide the user with tools (e.g., such as the selectable options 306 307) that allow the user to interact with the modelled version of the brain. The user can provide input for selecting portions of the processed data 302 to be displayed. The selected portions can be objects, e.g. brain parcellations about which the medical professional desires to see more information. Further a user may want to simulate removal of parcellation(s) from the brain. The user can specify particular portions of the brain to analyze. The user may also desire to identify and specify, on the GUI 300, particular objects on several features, such as local properties of brain tissue, parcellation parameters, structural markers, functional markers, and the like. The disclosed technology therefore can provide the user with a more comprehensive, interactive, and user-friendly interface for making determinations about a particular brain's condition(s).

The user can use the selectable options 306-307 to specify particular actions (e.g. by making selections in the GUI 300 presented at the user device 104 via an input device) with regards to the processed data 302. For example, the user can select to visualize left, right, or both sides of the brain for anatomical, parcellation information, and/or grouping information of parcellations using the GUI 300. As another example, the user can select to only visualize specified functional, structural and/or parcellation data. Such data can represent volume(s) beneath the surface of the brain.

The user can also choose options to export the processed data 302, for example, using an available network. The user can save the exported data (e.g., in the data store 108 in FIG. 1), which can be used in future research and analysis.

The GUI 300 presents only some options that may be presented to the user with regards to the processed data 302.

One or more other options are also possible and can be presented in the GUI 300 and/or in additional GUIs that are displayed at the user device 104.

Moreover, as described herein, the GUI 300 can be part of a specialized computing system in the hospital IT infrastructure. Sometimes, the GUI 300 can also be accessible via a web browser. The GUI 300 may be configured, e.g. by authentication mechanisms such as login using username and/or password, biometric detection, and/or the like, to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 300 can also be in communication with or otherwise linked to one or more external devices, such as remote computers, that can be used to facilitate brain surgery or other medical procedures.

FIG. 4 is an example user-interactive GUI displaying the grouped parcellations. The GUI 400 can display visual representations of the brain including anatomical information 430 and information of the grouped parcellations 440, simultaneously. The grouping information can include one or more group names 450 according to a brain function or another brain characteristic, e.g., a disease, a symptom. As shown in FIG. 4, the group names 450 include "memory," "planning," "attention," etc. The grouping information can include a group label 460. One or more group labels 460 may correspond to a single group name 450. For example, the group name "executive function" can correspond to three different group labels 460. The grouping information can also include a plurality of parcellations that are grouped under a same group label and/or under the same group name. As shown in Table 1, each parcellation, e.g., grouped parcellation, may be associated with one or more group names 450, group labels 460, and group identifiers. In the cases where a single parcellation is associated with multiple group names or group identifiers, it can be grouped under multiple corresponding grouping categories or grouping levels.

The grouped parcellations 440 can be spatially aligned to anatomical structures 430 of the brain. The GUI 400 may allow a user to customize the anatomical structure 430 to be displayed with the grouped parcellations. For example, the user may interact with the selective options 407 to turn on/off displaying the glass brain as the anatomical information 430. When the glass brain is turned off, the anatomical information 430 can include medical images of the brain, e.g., MRI images of the brain from one or more different anatomical views, e.g., axial, coronal, and sagittal view. The anatomical information 430 can be displayed as a background and the grouped parcellations 440 can be superimposed thereon and in spatial alignment with the anatomical information 430.

The parcellations with a same group name 450 may be displayed using a uniform pattern, grayscale, and/or color. The parcellations of different group labels 460 under the same group name 450 may be displayed using a uniform pattern, grayscale, and/or color. Alternatively, the parcellations of different group labels 460 may be displayed using different patterns, grayscales, and/or colors. The different group names 450 and/or group labels 460 and their corresponding pattern, grayscale, and/or color can be included in the legend for convenient reference by the user. A representation 470, e.g., a white circle with text showing the group names 450 or group label 460, can be superimposed on the grouped parcellations 440 and the anatomical information 430. Such representation 470 can include some or all information of the group name 450, information of the group label 460, or their combinations.

The user may interact with the selectable options 407 to select a specific view of the brain. When the interaction is received, the display of the grouped parcellations 440 can be adjusted accordingly to display parcellations in groups in the selected view. As shown in FIG. 4, the grouped parcellations 440 are shown as an overlay on a sagittal image of the brain and also spatially registered with a coronal image and an axial image of the brain.

Continuing to refer to FIG. 4, the groups of parcellations that are involved in different cognitive functions can be spatially distinct from each other. The group of parcellations that is associated with memory is located to the posterior side of the brain, while the group of parcellations that is associated with "planning" function is located on the anterior side of the brain, in relatively close proximity to the group involved in "attention." One or more groups include parcellations that are spatially adjacent to or connected with other parcellations in the same group. In some cases, a group may include parcellation(s) that are not spatially adjacent to, or connected with, other parcellations in the same group.

The user may interact with the selectable options 406 to select other data, e.g., tractography data 480 that can be simultaneously displayed with the grouped parcellation data 440. Such tractography data 480 are represented with lines connecting voxels or parcellations. The tractography data 480 may indicate intragroup connectivity among parcellations or voxels within the same group. Similarly, the tractography data 480 may indicate intergroup connectivity among different groups. The quantity of tracts and/or color or grayscale of the tracts may indicate the degree of connectivity.

Additionally, in response to detecting a user interaction with the GUI 400, for example, with one or more parcellations displayed on the GUI, a pop-up window with one or more parameters or metrics related to the selected parcellation can be displayed on the GUI 400. Such parameters may be overlaid on the visual representations of the particular brain. The pop-up window can be in proximity to the selected parcellations on the GUI. The user may interact with the pop-up window to drag it to a different position, delete it, or click on one or more parameters listed thereon. In response to detecting a user interaction with the pop-up window, e.g., with a hyperlink in the pop-up window, the GUI 400 can display a second window that includes additional parameters or metrics related to the user selection of parcellations or groups of parcellations. The second window can be in a separate window from the GUI 400.

The parameters and metrics can be part of, and included in, parcellation data 440. The parameters and metrics can include but are not limited to: a parcellation ID, MNI coordinates of a parcellation, a parcellation label, a group name, a group identifier, a percentage overlap of the parcellation, or their combinations. The percentage overlap value can indicate a percentage that the parcellation may overlap with the user-selected group of brain function or characteristics. The percentage overlap may but is not required to exceed a pre-determined threshold. The parameters and metrics may include a list of parameters and metrics, each parameter or metric including a name of parameter, a value of the parameter, with or without a unit.

Figure 5:
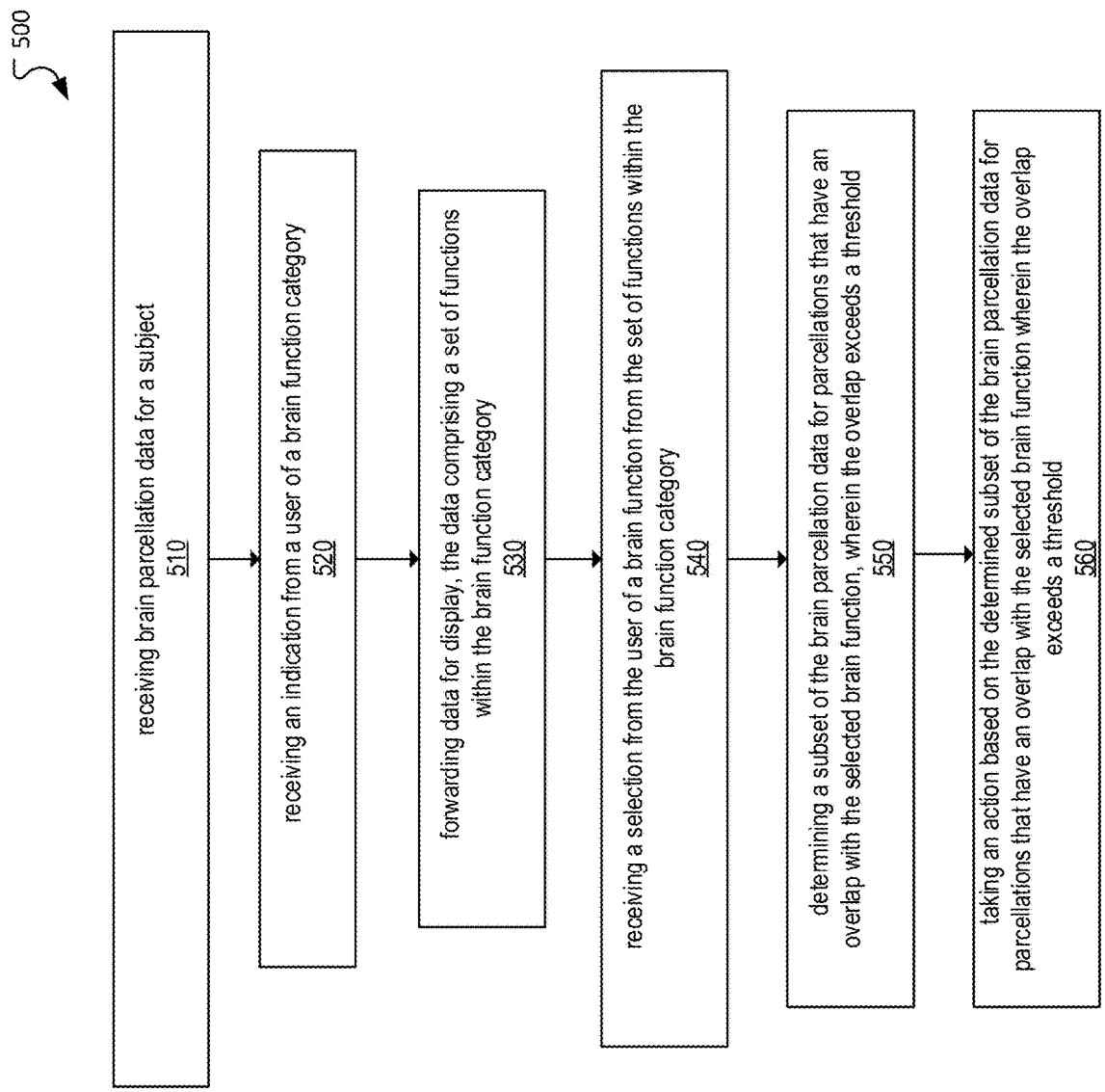
FIG. 5 illustrates an example process for enabling the user-interactive GUI to display grouping of parcellations of the brain.

FIG. 5 is an example process of grouping parcellations and enabling visualization of grouped parcellation. The operations in the process of grouping parcellations 500 may be performed by the computer system 106 in FIGS. 1-2. The computer system may receive parcellation data of the brain of a subject (510). Such data can be received from another computer or memory device such as the data store 108 in FIGS. 1-2. The parcellation data can be from some or all portions of the brain. The parcellation data, for one or more parcellations, may include a parcellation ID, a parcellation label, MNI space coordinates, as shown in Table 1. The parcellation label and the parcellation ID can each be used as a unique identifier of the parcellation. The parcellation data can be spatially registered relative to anatomical data of the same brain. The registration can be performed by the computer system 106 in FIGS. 1-2. The anatomical data can include one or more brain images, either raw or processed. The anatomical data can include a glass brain.

The computer system can receive an indication from a user of a brain function category or other brain characteristics category 520. The brain function category or characteristics category can include a set of functions or characteristics. In some cases, the category may include only one or more than one functions or characteristics in the set. As an example, a brain function category can be cognitive and it can include a set of functions including one or more functions selected from but not limited to: memory, language, attention, association, orientation, planning, and executive functions. Each of these functions may include one or more sub-functions. As another example, a brain function category can be a mood or an emotion, and its set of functions can include but is not limited to sadness, happiness, hopelessness, anxiety, stress, fear, anger, pride, eagerness, sense of loss, motivation, shock, and confusion. As another example, a brain characteristics category can be a brain disease, e.g., depression, and a set of characteristics can include one or more selected from: sadness, anxiety, guilt, anger, mood swings, and irritability. As yet another example, a brain characteristics category can be a feeling, e.g., fear or threat, and include one or more characteristics associated with the feeling, such as potential threat and persistent threat. In some cases, a category can include response to threat, fear, stress, anxiety, and reward. In other words, the brain category can include 1) emotions: 2) scholastic abilities; 3) symptoms; 5) diseases; 4) ability to do certain types of work; or 5) an answer to a question, e.g., a clinical question that is important in neuropsychological research or diagnosis and that is not addressed by categories 1-4.

In some embodiments, the brain function category received from the user is pre-stored in the computer system 106 or in another device such as the data store 108 in a hierarchy with one or more levels, each level becoming more specific. As such, the computer system can use the user-selected brain function category to locate a set of brain functions assigned to that category. The set of brain functions may be at a single grouping level. Alternatively, the set of brain functions may be at multiple group levels, and one of them at a first level can include one or more subfunctions at a second level lower than the first level. As an example, a brain function category can be scholastic abilities, and such category can include multiple functions at a first level, such as problem solving, language, organization, time management, creativity, independent learning, collaboration, and science, technology, engineering, and mathematical (STEM) abilities. And the "language" function can include on a next lower level, reading, writing, and verbal communication. As another example, the function category can be "reward." At a next lower level, there can be different functions such as "reward anticipation," "reward satiation," and "reward receipt."

The computer system may forward the data comprising a set of functions within the user-selected category for display 530. Such data can be pre-stored in the computer system or in the data store as shown in FIG. 1. The data can be stored with a mapping relationship so that a set of functions or characteristics can be located via mapping based on the user selected brain function category or other brain characteristic category. As an example, in response to determining that the user selected "cognitive functions" as the category in 520, the computer system may forward a list of cognitive functions for display 530.

The computer system may receive a selection from the user of one or more brain functions from the set of functions within the brain function category 540. As an example, the selection from the user may include only "memory" in the cognitive category. As another example, the user may select "memory," "planning," and "attention" in the cognitive category. Such selection may be via an input device with the GUI. For example, the user may use a mouse, a touch screen to check or otherwise indicate what functions or characteristics he/she wants to select. Alternatively, the user may give an audio input that can be recognized by the computer system to make a selection.

In some cases, the set of functions within the brain function category comprises a hierarchy of multiple levels, and each level comprises one or more brain functions in the set of functions. A first brain function or characteristics on a first level in the hierarchy can include at least a second brain function on a second level lower than the first level. As an example, a first brain function on a first level, e.g., cognitive function, in the hierarchy comprises at least a second brain function on a second level lower than the first level, e.g., language (as shown in Table 2). In some cases, the function "language" can further be assigned to a third level which can include, for example, language fluency, reading, writing, and comprehension (as shown in Table 2). In some cases, the hierarchy includes only one level. In other cases, the hierarchy includes at least two different levels with the first level being higher than the second level.

The computer system can determine some or all of the brain parcellation data that have an overlap with the user-selected brain function(s) or characteristics, where the overlap exceeds a threshold 550. As an example, the computer system can determine a group cluster ID (as shown in Table 1), a group name (as shown in Table 1), or any other identifier contained in the parcellation data and see if a parcellation overlaps with the user-selected function or characteristics. For example, when the user-selected function is "fear," the computer system can locate parcellation IDs 279, 302, 368, 320 because these parcellations have a group name and or a group cluster ID that partially matches the user selection of "fear." The computer system additionally determines how much overlap each parcellation may have with the user selection, for example, by determining the percentage value of overlap (as in Table 1). The computer system can then compare the overlap value with a threshold to determine whether a particular parcellation should be included in the subset that overlaps with the selected brain function or not. The percentage value of overlap can be related to grouping that is based on RDoC defined regions. The RDoC defined regions can include spherical volumes, e.g., clusters, within the MNI space, and the percentage overlap between the RDoC clusters and the parcellations can be determined. The percentage of overlap can be calculated in customized ways. For example, it can be calculated as a volume of the parcellation that falls within the RDoC sphere divided by the total volume of parcel's region of interest. In other words, the percentage of overlap may indicate what percentage of each parcellation falls within the corresponding RDoC sphere. The percentage overlap may also be obtained by calculating a coefficient indicative of similarity between the corresponding RDoC sphere(s) and the parcel, e.g., the Dice's coefficient.

The threshold can be predetermined by the computer system based on empirical data or user input. The threshold can be determined based on expert knowledge of healthy brains, diseased brains, or both. As an example, the threshold can be calculated by the computing system automatically using a computer program or software based on multiple subjects as its input(s). The threshold can be inferred using a trained machine learning algorithm. The threshold can be calculated in various ways. As an example, the threshold can be calculated across a population of subjects. As another example, the threshold can be calculated in comparison to values for that particular subject, e.g., the threshold can be set as above top 10% of overlap percentage values within a specified region of the brain of the subject. As yet another example, the threshold can also be calculated based on a standard deviation from the overlap percentage values of the particular subject, of some or all portions of the brain. The threshold can also be a function of the patient information including but not limited to age, gender and other biological factors.

In some implementations, the computer system can determine some or all of the brain parcellation data that have an overlap with the user-selected brain function(s) or characteristics based on existing testing information (as shown in Table 2), MRI image analysis, or otherwise available measurements. As shown in Table 2 below, the computer system can determine a brain function category (as shown in Table 2), a brain function within the brain function category (as shown in Table 2), or any other identifier contained in the parcellation data and see if a parcellation overlaps with the user-selected function or characteristics. For example, when the user-selected brain function is "motor," or "hand motor," the computer system can locate parcellation labeled as "L_4," because this parcellation have a function category name and/or function name that at least partially matches the user selection. The computer system may additionally determine how this parcellation overlaps with the user selection, for example, by determining how this parcellation responded to a corresponding test (as in Table 2). If this parcellation has been identified during the corresponding test as linking to the selected brain function, e.g., with an uncertainty below a threshold, this parcellation can be included in the subset that overlaps with the selected brain function. Alternatively, this parcellation can be identified from fMRI analysis or other clinical measurement as linked to the selected brain function.

TABLE 2

Exemplary grouped parcellations in association with cognitive functions.

| Function Category | Function | Corresponding Test | Parcellation Label |
|---|---|---|---|
| Motor | Hand motor | ['Finger tapping', 'Grooved pegboard test'] | L_4 |
| Language | Fluency | ['QAB'] | L_44 |
| Language | Comprehension | ['QAB'] | L_STSdp |
| Language | Writing | ['QAB'] | L_6ma |
| Memory | Verbal | ['California verbal learning', 'Hopkins verbal learning (2 parts)'] | R_TE1a |

The computer system can then take an action on the determined subset of the brain parcellation data that have an overlap with the brain function where the overlap exceeds a threshold 560. The action can be to display the determined subset of the brain parcellation data using the GUI. The display can include spatially registered anatomical data and the parcellation data. The parcellation data can be superimposed on the anatomical data.

After the determined subset of parcellation data is displayed at the user computer, for example, using a digital display, the user may interact with the data via a user-interactive GUI at the digital display of the user computer. The computer system can receive user interaction(s) with the GUI to customize display of the parcellation data. For example, the user may adjust the display to be different views of the brain image data and the determined subset of brain parcellation data.

At 560, the computer system may analyze the determined subset of parcellation data and provide the user corresponding results so that the user can make a recommendation or decision regarding a treatment, a diagnosis, or otherwise a clinical decision.

In some cases, at 560, the computer system may forward the determined subset of the brain parcellation data for display at a user device; and receive an export request of the determined subset of the brain parcellation data, or both. The computer system may export the determined subset of brain parcellation data to another device for display or further processing and analysis. For example, the computer system may export the data to a surgical guidance system and then can be used by a medical professional for providing surgical guidance. As another example, the computer system may export the data to another computer so that the data can be compared with data from different subjects or patients.

Figure 6:
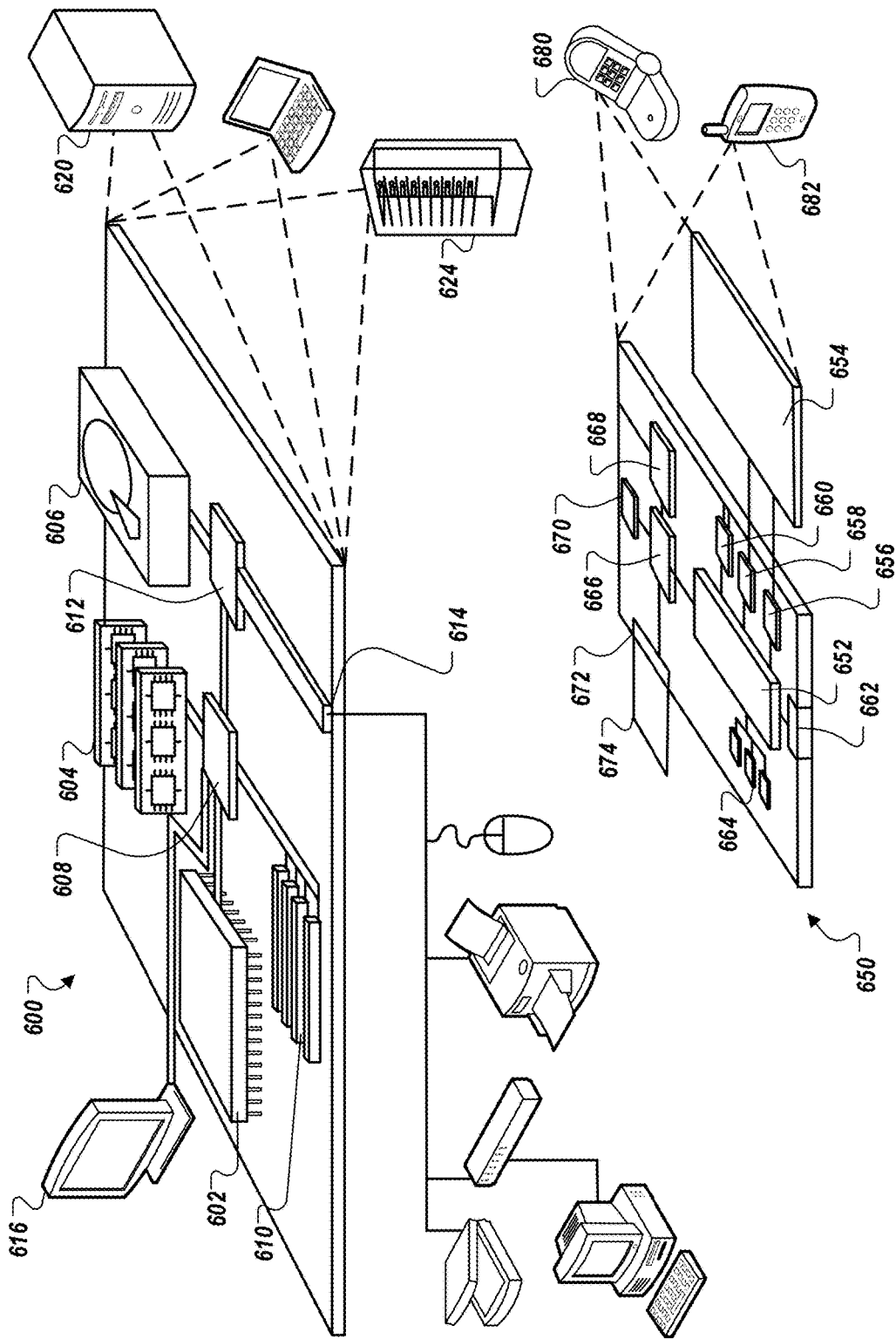
FIG. 6 is a schematic diagram that shows an example of a computing device and a mobile computing device.

FIG. 6 shows an example of a computing device 600 and an example of a mobile computing device that can be used to implement the techniques described here. The computing device 600 can be the computer system 106 or user device 104 in FIGS. 1-2. The computing device 600 can be various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and can be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 604 stores information within the computing device 600. The memory 604 can also be another form of computer-readable medium, such as a magnetic or optical disk.

The storage device 606 is capable of providing mass storage for the computing device 600. In some implementations, the storage device 606 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 604, the storage device 606, or memory on the processor 602.

The high-speed interface 608 manages bandwidth-intensive operations for the computing device 600, while the low-speed interface 612 manages lower bandwidth-intensive operations. Such allocation of functions is exemplary only.

The computing device 600 can be implemented in a number of different forms. For example, it can be implemented as a standard server 620, or multiple times in a group of such servers. In addition, it can be implemented in a personal computer such as a laptop computer 622. It can also be implemented as part of a rack server system 624. Alternatively, components from the computing device 600 can be combined with other components in a mobile device (not shown), such as a mobile computing device 650. Each of such devices can contain one or more of the computing device 600 and the mobile computing device 650, and an entire system can be made up of multiple computing devices communicating with each other.

The mobile computing device 650 includes a processor 652, a memory 664, an input/output device such as a display 654, a communication interface 666, and a transceiver 668, among other components. The mobile computing device 650 can also be provided with a storage device, such as a micro-drive or other device, to provide additional storage. Each of the processor 652, the memory 664, the display 654, the communication interface 666, and the transceiver 668, are interconnected using various buses, and several of the components can be mounted on a common motherboard or in other manners as appropriate.

The processor 652 can execute instructions within the mobile computing device 650, including instructions stored in the memory 664. The processor 652 can communicate with a user through a control interface 658 and a display interface 656 coupled to the display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can provide communication with the processor 652, so as to enable near area communication of the mobile computing device 650 with other devices. The external interface 662 can provide, for example, for wired communication in some implementations, or for wireless communication in other implementations, and multiple interfaces can also be used.

The memory 664 stores information within the mobile computing device 650. The memory 664 can be implemented as one or more of a computer-readable medium or media, a volatile memory unit or units, or a non-volatile memory unit or units.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 664, the expansion memory 674, or memory on the processor 652. In some implementations, the computer program product can be received in a propagated signal, for example, over the transceiver 668 or the external interface 662.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the computing system can be cloud based and/or centrally processing data. In such cases, anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
   receiving, at one or more processors, brain parcellation data for a subject;
   receiving, from a user device, an indication of a brain function category;
   forwarding brain function data for display, via a graphical user interface on the user device, the data comprising a set of brain functions within the brain function category;
   receiving, from the user device, a selection of a brain function from the set of brain functions within the brain function category, wherein the set of brain functions within the brain function category comprises a hierarchy of multiple levels, and each level comprises one or more brain functions in the set of brain functions and wherein a first brain function on a first level in the hierarchy comprises at least a second brain function on a second level lower than the first level in the hierarchy;
   determining a subset of the brain parcellation data for parcellations that have a volume overlap with the selected brain function where the volume overlap exceeds a threshold, wherein the determining comprises:
     determining selected brain function defined regions that are active in performing the selected brain function, the selected brain function defined regions having specified volumes, wherein determining a subset of the brain parcellation data for parcellations that have an overlap with the selected brain function comprises determining a volume of a parcellation that falls within the specified volume of a selected brain function defined region;
   modeling the determined subset of the brain parcellation data onto a representation of a brain to produce modeled brain data;
   forwarding the modeled brain data for display via a graphical user interface at a user device; and
   taking an action based on the determined subset of the brain parcellation data for parcellations that have an overlap with the selected brain function where the overlap exceeds a threshold.

2. The method of claim 1, wherein the brain function category is one or more selected from: an emotion, scholastic ability, a brain disease symptom, ability to perform one or more predetermined types of work, and an answer to one or more clinical questions.

3. The method of claim 1, wherein taking the action based on the determined subset of the brain parcellation data comprises:
   forwarding the determined subset of the brain parcellation data for display at a user device;
   receiving an export request of the determined subset of the brain parcellation data; or both.

4. The method of claim 1, wherein taking the action based on the determined subset of the brain parcellation data comprises:
   analyzing the determined subset of the brain parcellation data; and
   allowing a user to make a recommendation regarding a treatment based on the analysis of the determined subset of the brain parcellation data.

5. The method of claim 1, wherein taking the action based on the determined subset of the brain parcellation data comprises:
   analyzing the determined subset of the brain parcellation data; and
   making a recommendation regarding a treatment based on the analysis of the determined subset of the brain parcellation data.

6. The method of claim 1, wherein taking the action based on the determined subset of the brain parcellation data comprises:
   analyzing the determined subset of the brain parcellation data.

7. The method of claim 1, wherein the brain parcellation data for the subject comprises a plurality of parcellations, and wherein the plurality of parcellations are spatially registered to brain anatomical data of the subject.

8. The method of claim 1, wherein the method further comprises receiving modeled brain data interaction input reflecting an interaction by the user with the modeled brain data and forwarding data representing a rotated view of the modeled brain data to the user device in response to receipt of the modeled brain data interaction input.

9. The method of claim 1, wherein taking an action comprises receiving an input reflecting simulated removal of a user-selected parcellation and outputting updated modeled brain data resulting from removing the user-selected parcellation.

10. The method of claim 8, wherein the brain function category is selected from: response to threat, fear, stress, anxiety, and reward.

11. The method of claim 1, wherein the brain is represented by a brain atlas comprising a set of three-dimensional voxels representing at least a portion of the brain, each voxel assigned to one of the parcellations in a parcellation scheme, each selected brain function defined region comprising a plurality of parcellations, the parcellation being assigned to a first grouping and to a second subgrouping within the first grouping.

12. The method of claim 1, wherein the threshold is determined based on expert knowledge of healthy brains, diseased brains, or both.

13. The method of claim 1, wherein the determined subset of the brain parcellation data comprises one or more parcellations within the brain parcellation data and corresponding spatial information of the one or more parcellations within a brain of the subject.

14. The method of claim 1, wherein forwarding the data for display comprises sending the data for display using a graphic user interface, and wherein the selection from the user of the brain function from the set of functions within the brain function category is made by using the graphic user interface.

15. The method of claim 1, wherein the overlap with the selected brain function comprises a percentage value.

16. The method of claim 15, wherein the percentage value is calculated based on research domain criteria (RDoC) defined regions.

17. The method of claim 1, wherein brain parcellation data comprises, for one or more parcellations, a corresponding brain function category, a sub-category of the corresponding brain function category, a unique identifier of the one or more parcellation, or a set of coordinates.

18. A computer program product, encoded on one or more non-transitory computer storage media, comprising instructions that when executed by one or more computers cause the one or more computers to perform operations comprising:
receiving, at one or more processors, brain parcellation data for a subject;
receiving, from a user device, an indication of a brain function category;
forwarding brain function data for display, via a graphical user interface on the user device, the data comprising a set of brain functions within the brain function category;
receiving, from the user device, a selection of a brain function from the set of functions within the brain function category, wherein the set of brain functions within the brain function category comprises a hierarchy of multiple levels, and each level comprises one or more brain functions in the set of brain functions and wherein a first brain function on a first level in the hierarchy comprises at least a second brain function on a second level lower than the first level in the hierarchy;
determining a subset of the brain parcellation data for parcellations that have a volume overlap with the selected brain function where the volume overlap exceeds a threshold, wherein the determining comprises:
determining selected brain function defined regions that are active in performing the selected brain function, the selected brain function defined regions having specified volumes, and wherein determining a subset of the brain parcellation data for parcellations that have an overlap with the selected brain function comprises determining a volume of a parcellation that falls within the specified volume of a selected brain function defined region;
modeling the determined subset of the brain parcellation data onto a representation of a brain to produce modeled brain data;
forwarding modeled brain data for display via a graphical user interface at a user device; and
taking an action based on the determined subset of the brain parcellation data for parcellations that have an overlap with the selected brain function where the overlap exceeds a threshold.

19. One or more non-transitory computer storage media encoded with computer program instructions that when executed by one or more computers cause the one or more computers to perform operations comprising:
receiving, at one or more processors, brain parcellation data for a subject;
receiving, from a user device, an indication of a brain function category;
forwarding brain function data for display, via a graphical user interface on the user device, the data comprising a set of brain functions within the brain function category;
receiving, from the user device, a selection of a brain function from the set of brain functions within the brain function category, wherein the set of brain functions within the brain function category comprises a hierarchy of multiple levels, and each level comprises one or more brain functions in the set of brain functions and wherein a first brain function on a first level in the hierarchy comprises at least a second brain function on a second level lower than the first level in the hierarchy;
determining a subset of the brain parcellation data for parcellations that have a volume overlap with the selected brain function where the volume overlap exceeds a threshold, wherein the determining comprises:
determining selected brain function defined regions that are active in performing the selected brain function, the selected brain function defined regions having specified volumes, and wherein determining a subset of the brain parcellation data for parcellations that have an overlap with the selected brain function comprises determining a volume of a parcellation that falls within the specified volume of a selected brain function defined region;
modeling the determined subset of the brain parcellation data onto a representation of a brain to produce modeled brain data;
forwarding the modeled brain data for display via a graphical user interface at a user device; and
taking an action based on the determined subset of the brain parcellation data for parcellations that have an overlap with the selected brain function where the overlap exceeds a threshold.

20. A system comprising:
one or more computers and one or more storage devices on which are stored instructions that are operable, when executed by the one or more computers, to cause the one or more computers to perform operations comprising:
receiving, at one or more processors, brain parcellation data for a subject;
receiving, from a user device, an indication of a brain function category;
forwarding brain function data for display, via a graphical user interface on the user device, the data comprising a set of brain functions within the brain function category;
receiving, from the user device, a selection of a brain function from the set of brain functions within the brain function category, wherein the set of brain functions within the brain function category comprises a hierarchy of multiple levels, and each level comprises one or more brain functions in the set of brain functions and wherein a first brain function on a first level in the hierarchy comprises at least a second brain function on a second level lower than the first level in the hierarchy;

determining a subset of the brain parcellation data for parcellations that have a volume overlap with the selected brain function where the volume overlap exceeds a threshold, wherein the determining comprises:

determining selected brain function defined regions that are active in performing the selected brain function, the selected brain function defined regions having specified volumes, and wherein determining a subset of the brain parcellation data for parcellations that have an overlap with the selected brain function comprises determining a volume of a parcellation that falls within the specified volume of a selected brain function defined region;

modeling the determined subset of the brain parcellation data onto a representation of a brain to produce modeled brain data;

forwarding the modeled brain data for display via a graphical user interface at a user device; and taking an action based on the determined subset of the brain parcellation data for parcellations that have an overlap with the selected brain function where the overlap exceeds a threshold.

\* \* \* \* \*